US008658836B2

(12) United States Patent
Benitez et al.

(10) Patent No.: US 8,658,836 B2
(45) Date of Patent: Feb. 25, 2014

(54) OXIDATION OF HYDROCARBONS

(75) Inventors: Francisco M. Benitez, Houston, TX (US); Jihad M. Dakka, Whitehouse Station, NJ (US); Edmund J. Mozeleski, Califon, NJ (US); Stephen Zushma, Clinton, NJ (US); John Scott Buchanan, Lambertville, NJ (US); Jon E. Stanat, Westhampton Beach, NY (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 380 days.

(21) Appl. No.: 12/678,419

(22) PCT Filed: Oct. 8, 2008

(86) PCT No.: PCT/US2008/079172
§ 371 (c)(1),
(2), (4) Date: May 17, 2010

(87) PCT Pub. No.: WO2009/058531
PCT Pub. Date: May 7, 2009

(65) Prior Publication Data
US 2010/0228047 A1    Sep. 9, 2010

Related U.S. Application Data

(60) Provisional application No. 60/984,271, filed on Oct. 31, 2007, provisional application No. 61/045,819, filed on Apr. 17, 2008.

(51) Int. Cl.
*C07C 409/00* (2006.01)
(52) U.S. Cl.
USPC .......................................... 568/569; 568/570

(58) Field of Classification Search
None
See application file for complete search history.

(56) References Cited

U.S. PATENT DOCUMENTS

| | | | |
|---|---|---|---|
| 3,418,256 A | 12/1968 | Rigney et al. | |
| 3,959,381 A | 5/1976 | Arkell et al. | |
| 4,136,123 A | 1/1979 | Hutchings | |
| 4,255,592 A | 3/1981 | Kawai et al. | |
| 4,282,383 A | 8/1981 | Dai et al. | |
| 4,450,303 A | 5/1984 | Drake | |
| 5,030,739 A | 7/1991 | Foricher et al. | |
| 5,166,454 A | 11/1992 | Harandi et al. | |
| 5,298,667 A | 3/1994 | Iwanaga et al. | |
| 5,405,814 A | 4/1995 | Beech, Jr. et al. | |
| 5,981,420 A | 11/1999 | Nakano et al. | |
| 6,291,718 B1 | 9/2001 | Matsui et al. | |
| 1,074,537 A1 | 3/2003 | Miura et al. | |
| 1,331,215 A1 | 1/2004 | Sugahara | |
| 6,720,462 B2 | 4/2004 | Kuhnle et al. | |
| 6,852,893 B2 * | 2/2005 | Kuhnle et al. | 568/314 |
| 7,038,089 B2 * | 5/2006 | De Frutos Escrig et al. | 568/564 |
| 7,326,815 B2 | 2/2008 | Dakka et al. | |
| 1,862,442 A1 | 10/2008 | Kajikawa et al. | |
| 2002/0169331 A1 | 11/2002 | Miura et al. | |
| 2003/0083527 A1* | 5/2003 | Kuhnle et al. | 568/385 |
| 2004/0162448 A1 | 8/2004 | Yang et al. | |
| 2004/0236152 A1 | 11/2004 | Black et al. | |
| 2005/0043559 A1 | 2/2005 | Marhold et al. | |
| 2005/0167658 A1 | 8/2005 | Williams et al. | |
| 2007/0265476 A1 | 11/2007 | Dakka et al. | |
| 2010/0222609 A1 | 9/2010 | Dakka et al. | |

FOREIGN PATENT DOCUMENTS

| | | |
|---|---|---|
| DE | 2 300 903 | 1/1973 |
| EP | 1 074 536 | 2/2001 |
| EP | 1 088 807 | 4/2001 |
| EP | 1 088 809 | 4/2001 |
| EP | 1088809 | * 4/2001 |
| JP | 62-114922 | 5/1987 |
| JP | 11-180913 | 7/1999 |
| JP | 11180913 | * 7/1999 |
| JP | 2001-192354 | 7/2001 |
| JP | 2004-035460 | 2/2002 |
| JP | 2002-282698 | 10/2002 |
| WO | 94/20213 | 9/1994 |
| WO | 99/47485 | 9/1999 |

| WO | 2006/015826 | 2/2006 |
| WO | 2008/037435 | 4/2008 |
| WO | 2009/025939 | 2/2009 |

OTHER PUBLICATIONS

Machin translation of JP 11180913.*
Ishii et al., Catalyst Today, 117 (2006) 105-113.*
Arends et al., Tetrahedron (2002), 58(44), 9055-9061.*
J. Howard et al., "*Absolute Rate Constants for Hydrocarbon Oxidation. XI. The Reactions of Tertiary Peroxy Radicals[1,2]*", Canadian Journal of Chemistry, 1968, vol. 47, pp. 2656-2660.
J. Howard et al., "*Absolute Rate Constants for Hydrocarbon Oxidation. VIII. The Reactions of Cumylperoxy Radicals[1]*", Canadian Journal of Chemistry, 1968, vol. 46, pp. 1018-1022.
J. Howard, "Absolute Rate Constants for Hydrocarbon Autoxidation. XXII. The Autoxidation of Some Vinyl Compounds[1]", Canadian Journal of Chemistry, 1972, vol. 50, pp. 2298-2304.
J. Howard et al., "*Absolute Rate Constants for Hydrocarbon Autoxidation. XV. The Induced Decomposition of Some T-Hydroperoxides[1]*", Canadian Journal of Chemistry, 1969, vol. 47, pp. 3797-3801.
J. Howard et al., "*Absolute Rate Constants for Hydrocarbon Autoxidation. XIV. Termination Rate Constants for Tertiary Peroxy Radicals[1]*", Canadian Journal of Chemistry, 1969, vol. 47, pp. 3793-3795.
Y. Ishii et al., "*Recent Progress in Aerobic Oxidation of Hydrocarbons by N-Hydroxyimides*", Catalysis Today, 2006, vol. 117, pp. 105-113.
T. Iwahama et al., "*Aerobic Oxidation of Alcohols to Carbonyl Compounds Catalyzed by N-Hydroxyphthalimide (NHPI) Combined with Co (acac)$_3$*", Tetrahedron Letters, 1995, vol. 36, No. 38, pp. 6923-6926.
J. Kochi, "*Chemistry of Alkoxy Radicals: Cleavage Reactions*", Journal of the American Chemical Society, 1962, vol. 84, pp. 1193-1197.
S. Sakaguchi et al., "*Oxidation of Organic Substrates with Molecular Oxygen Catalyzed by Vanadomolybdophosphate (NPV$_6$Mo$_6$) Combined with N-Hydroxyphthalimide (NHPI)*", Technology Reports of Kansai University, 1996, No. 38, pp. 123-131.
R. Sheldon et al., "*Organocatalytic Oxidations Mediated by Nitroxyl Radicals*", Advanced Synth. Catal., 2004, vol. 346, pp. 1051-1071.
Y. Yen, "*Phenol*", Process Economics Report No. 22B, Stanford Research Institute, 1977, pp. 113-121, 261 and 263.
Iwahama T., et al. "*Aerobic Oxidation of Alcohols to Carbonyl Compounds Catalyzed by n-hydroxyphthalimide (NHPI) Combined with Co (acac)3*", Tetrahedron Letters, Sep. 18, 1995, V. 36, No. 38, pp. 6923-6926.

Sakaguchi S., et al, "*Oxidation of Organic Substrates with Molecular Oxygen Catalyzed by Vanadomolybdophosphate (NPV6M06) Combined with N-Hydroxphtalimide (NHPI)*", Technology Reports of Kansai University, Osaka, JP, Mar. 1, 1996, No. 38, pp. 123-131.

* cited by examiner

*Primary Examiner* — Karl J Puttlitz
(74) *Attorney, Agent, or Firm* — Jamie L. Sullivan; Siwen Chen

(57) ABSTRACT

In a process for oxidizing a hydrocarbon to the corresponding hydroperoxide, alcohol, ketone, carboxylic acid or dicarboxylic acid, a reaction medium comprising a hydrocarbon is contacted with an oxygen-containing gas in the presence of a catalyst comprising a cyclic imide of the general formula (I):

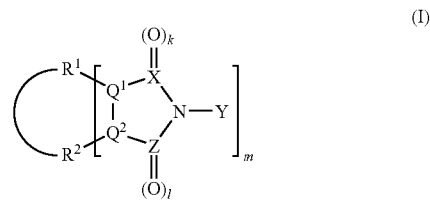

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I provided that $R^1$ and $R^2$ can be linked to one another via a covalent bond; each of $Q^1$ and $Q^2$ is independently selected from C, CH, N, and $CR^3$; each of X and Z is independently selected from C, S, $CH_2$, N, P and an element of Group 4 of the Periodic Table; Y is O or OH; k is 0, 1, or 2; l is 0, 1, or 2; m is 1 to 3; and $R^3$ can be any of the entities listed for $R^1$. The contacting is conducted under conditions such as to maintain the concentration of both water and organic acids in the reaction medium below 50 ppm.

15 Claims, 12 Drawing Sheets

OXIDATION OF HYDROCARBONS

CROSS-REFERENCE TO RELATED APPLICATIONS

This application is a National Stage Application of International Application No. PCT/US2008/079172 filed Oct. 8, 2008, which claims priority from USSN 60/984,271 filed Oct. 31, 2007 and 61/045,819 filed Apr. 17, 2008, all of which are incorporated herein by reference.

FIELD OF THE INVENTION

The present invention relates to a process for oxidizing hydrocarbons and, in particular, alkylaromatic hydrocarbons to produce for example phenol and substituted phenols.

BACKGROUND OF THE INVENTION

The oxidation of hydrocarbons is an important reaction in industrial organic chemistry. Thus, for example, the oxidation of cyclohexane is used commercially to produce cyclohexanol and cyclohexanone, which are important precursors in the production of nylon, whereas oxidation of alkylaromatic hydrocarbons, such as cumene, is used to produce phenol, a precursor in the production of polycarbonates and epoxy resins.

Oxidation of hydrocarbons can be conducted using well-known oxidizing agents, such as $KMnO_4$, $CrO_3$ and $HNO_3$. However, these oxidizing agents have the disadvantage of being relatively expensive, and moreover their use is accompanied by the production of unwanted coupling products which can represent disposal problems and ecological pollution.

Preferably, therefore, oxidizing agents based on peroxides or $N_2O$ are used. The cheapest oxidizing agent, however, is molecular oxygen, either in pure form or as atmospheric oxygen. However, oxygen itself is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds and hence a great number of industrial processes are based on the metal-catalyzed autooxidation of hydrocarbons. Thus, for example, the oxidation of cyclohexane with $O_2$ to cyclohexanol and/or cyclohexanone proceeds with the use of cobalt salts. These industrial processes are based on a free-radical chain mechanism, in which the bi-radical oxygen reacts with a hydrocarbon free radical, with formation of a peroxy radical and subsequent chain propagation by abstraction of an H atom from a further hydrocarbon. In addition to metal salts, however, organic molecules can also act as free-radical initiators.

However, it is a disadvantage of these processes that the selectivity decreases very greatly with increasing conversion and therefore the processes must be operated at a very low level of conversion. Thus, for example, the oxidation of cyclohexane to cyclohexanol/cyclohexanone is carried out at a conversion of 10 to 12% so that the selectivity is 80 to 85% ("Industrielle Organische Chemie" [Industrial Organic Chemistry] 1994, 261, VCH-Verlag, D-69451 Weinheim).

An alternative to metal salt catalysts is the use of organic mediators, for example N-hydroxyphthalimide (NHPI). Thus, U.S. Pat. Nos. 6,852,893 and 6,720,462 describe methods for oxidizing hydrocarbon substrates by contacting the substrate with an oxygen-containing gas, in which the oxygen content is from 5 to 100% by volume, in the presence of a free radical initiator and a catalyst, typically a N-hydroxycarbodiimide catalyst, such as N-hydroxyphthalimide (NHPI). The process is conducted at a temperature between 0° C. and 500° C. and a pressure between atmospheric and 100 bar (100 and 10,000 kPa). The molar ratio of the catalyst to the hydrocarbon substrate can range from $10^{-6}$ mol % to 1 mol %, whereas the molar ratio of free-radical initiator to the catalyst can be 4:1 or less, such as 1:1 to 0.5:1. Suitable substrates that may be oxidized by this process include cumene, cyclohexylbenzene, cyclododecylbenzene and sec-butylbenzene.

U.S. Pat. No. 7,038,089 discloses a process for preparing a hydroperoxide from a hydrocarbon selected from a group consisting of primary hydrocarbons, secondary hydrocarbons and mixtures thereof corresponding to said hydroperoxide which comprises conducting the oxidation of said hydrocarbon at a temperature in the range between 130 and 160° C. with an oxygen-containing gas in a reaction mixture containing said hydrocarbon and a catalyst comprising a cyclic imide compound and an alkali metal compound. Suitable hydrocarbons are said to include $C_4$ to $C_{20}$ tertiary alkanes (e.g., iso-butane, iso-pentane, iso-hexane, and the like), $C_7$ to $C_{20}$ (alkyl) aromatic hydrocarbons with 1 to 6 aromatic rings or $C_9$ to $C_{20}$ (cycloalkyl) aromatic hydrocarbons with 1 to 6 aromatic rings (e.g., xylene, cumene, ethylbenzene, diisopropylbenzene, cyclohexylbenzene, tetrahydronaphthalene (tetraline), indane, etc.), and the like. The amount of the cyclic imide compound used may be from 0.0001 to 1%, preferably from 0.0005 to 0.5%, by weight based on the reaction mixture, whereas the amount of the alkali metal compound may be from 0.000005 to 0.01%, preferably from 0.00001 to 0.005%, by weight based on the reaction mixture.

However, while N-hydroxycarbodiimides have shown activity and selectivity for the oxidation of hydrocarbons to products such as hydroperoxides, they suffer from the problem that they are readily hydrolyzed to non-catalytic species in the presence of the water and organic acids that tend to be generated as common by-products of the oxidation process. Moreover, under oxidation conditions, carbon-carbon bond scission reactions can generate alkyl radicals that can react with oxygen to terminate radical chain propagation and produce undesirable organic acids, such as low molecular weight organic acids eg containing 2, 3 or 4 carbon atoms, such as acetic acid. For example, acetic acid not only facilitates hydrolysis of N-hydroxycarbodiimides, but also catalyzes the exothermic decomposition of hydroperoxide products, which can result in dangerous temperature excursions as well as producing oxidation poisons.

According to the invention, it has now been found that the oxidation of alkylaromatic compounds in the presence of N-hydroxycarbodiimide catalysts can be facilitated by conducting the reaction under conditions such as to maintain the concentration of water and organic acids, especially low molecular weight organic acids, in the reaction medium below 50 ppm. It has been found that this can be achieved by judiciously operating the process at one or more conditions that maintain the water and organic acids below the mentioned levels, for example selected from low pressure and relatively high temperature and low oxygen concentration and by stripping water and organic acids from the reaction products as they are formed. The organic acids in question that are to be maintained below 50 ppm are of course not the target acids in the case where the reaction components are selected so that the target product is a relatively high molecular weight carboxylic acid or dicarboxylic acid. Rather they are the unwanted lower molecular weight organic acids.

SUMMARY OF THE INVENTION

In one aspect, the present invention resides in a process for oxidizing a hydrocarbon to an oxidized hydrocarbon product comprising the corresponding hydroperoxide, alcohol, ketone, carboxylic acid or dicarboxylic acid, the process comprising contacting a reaction medium comprising a hydrocarbon with an oxygen-containing gas in the presence of a catalyst comprising a cyclic imide of the general formula (I):

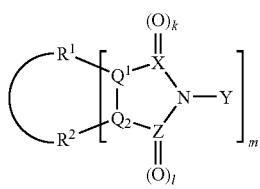

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that (ie in certain embodiments) $R^1$ and $R^2$ can be linked to one another via a covalent bond;
each of $Q^1$ and $Q^2$ is independently selected from C, CH, N, and $CR^3$;
each of X and Z is independently selected from C, S, $CH_2$, N, P and elements of Group 4 of the Periodic Table;
Y is O or OH;
k is 0, 1, or 2;
l is 0, 1, or 2;
m is 1 to 3; and
$R^3$ can be any of the entities (radicals, groups, or atoms) listed for $R^1$; and
wherein said contacting is conducted under conditions such as to maintain the concentration of water in the reaction medium below 50 ppm by weight and the concentration of organic acids in the reaction medium below 50 ppm by weight.

Conveniently, said hydrocarbon is an alkane or cycloalkane, such as isobutane or cyclohexane.

Alternatively, said hydrocarbon comprises at least one alkylaromatic compound of general formula (II):

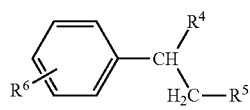

(II)

wherein $R^4$ and $R^5$ each independently represents hydrogen or an alkyl group having from 1 to 4 carbon atoms, provided that (ie in certain embodiments) $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group.

Conveniently, said alkylaromatic compound of general formula (II) is selected from ethyl benzene, cumene, sec-butyl-benzene, sec-pentylbenzene, p-methyl-sec-butylbenzene, 1,4-diphenylcyclohexane, sec-hexylbenzene, cyclohexyl-benzene and mixtures thereof. Typically, said alkylaromatic compound of general formula (II) is selected from cumene, sec-butylbenzene, cyclohexylbenzene and mixtures thereof.

Conveniently, said cyclic imide obeys the general formula (III):

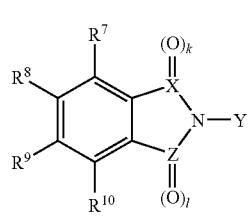

(III)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I;
each of X and Z is independently selected from C, S, $CH_2$, N, P and elements of Group 4 of the Periodic Table;
Y is O or OH;
k is 0, 1, or 2; and
l is 0, 1, or 2.

In one embodiment, said cyclic imide comprises N-hydroxyphthalimide (NHPI).

In a further aspect, the present invention resides in a process for producing a phenol, said process comprising:

(a) contacting a reaction medium comprising at least one alkylaromatic compound of general formula (II):

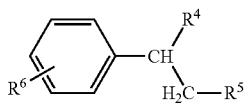

(II)

wherein $R^4$ and $R^5$ each independently represents hydrogen or an alkyl group having from 1 to 4 carbon atoms, provided that (ie in certain embodiments) $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group, with oxygen in the presence of a catalyst comprising a cyclic imide of the general formula (I):

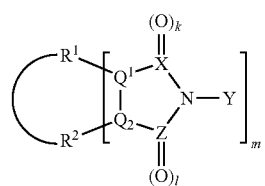

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that (ie in certain embodiments) $R^1$ and $R^2$ can be linked to one another via a covalent bond;

each of $Q^1$ and $Q^2$ is independently selected from C, CH, N, and $CR^3$;

each of X and Z is independently selected from C, S, $CH_2$, N, P and elements of Group 4 of the Periodic Table;

Y is O or OH;

k is 0, 1, or 2;

l is 0, 1, or 2;

m is 1 to 3; and $R^3$ can be any of the entities (radicals, groups, or atoms) listed for $R^1$, wherein said contacting is conducted under conditions such as to maintain the concentration of water in the reaction medium below 50 ppm by weight and the concentration of organic acids in the reaction medium below 50 ppm by weight and said contacting produces a hydroperoxide of general formula (IV):

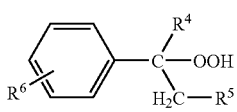

(IV)

in which $R^4$, $R^5$ and $R^6$ have the same meaning as in formula (II), and (b) converting the hydroperoxide of formula (IV) into a phenol and an aldehyde or ketone of the general formula $R^4COCH_2R^5$ (V), in which $R^4$ and $R^5$ have the same meaning as in formula (II).

Conveniently, said contacting is conducted at a relatively low pressure, for example below 300 kPa, such as between about 50 kPa and about 200 kPa. Preferably the pressure is in the range of from 75 to 150 kPa, more preferably from 80 to 130 kPa. The temperature of the contacting is conveniently maintained at a value, for example within the range of from 20° C. to 300° C., such as from 50° C. to 130° C. or 150° C. Preferably the temperature is maintained at a relatively high value such as in excess of 100° C. Most preferably the temperature is between about 105° C. and about 130° C.

Conveniently, said oxygen-containing gas comprises up to 21 volume %, for example from about 0.1 to about 21 volume %, oxygen.

Conveniently, a stripping gas is passed through said reaction medium during said contacting. In one embodiment, said stripping gas is the same as the oxygen-containing gas. In another embodiment, said stripping gas is different from the oxygen-containing gas and is inert to the reaction medium and the cyclic imide catalyst.

In all the above cases the operating conditions eg. low pressure, high temperature, stripping gas are selected to as to keep the levels of water and organic acid independently below 50 ppm by weight.

DETAILED DESCRIPTION OF THE EMBODIMENTS

Figure 1:
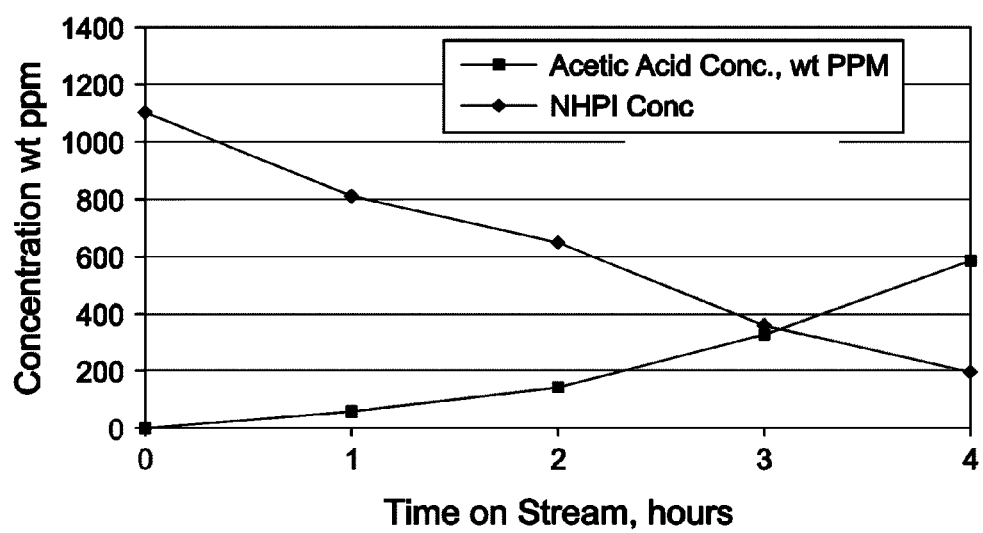
FIG. 1 is a graph plotting acetic acid and NHPI concentration against time on stream (T.O.S.) in the oxidation of sec-butylbenzene (SBB) in the initial presence of 0.11 wt % (1100 ppm) NHPI at 690 kPag (100 psig) according to the process of Example 1.

The terms "group", "radical", and "substituent" are used interchangeably in this document. For purposes of this disclosure, "hydrocarbyl radical" is defined to be a radical which contains hydrogen atoms and up to 20 carbon atoms and which may be linear, branched, or cyclic, and when cyclic, aromatic or non-aromatic. "Substituted hydrocarbyl radicals" are radicals in which at least one hydrogen atom in a hydrocarbyl radical has been substituted with at least one functional group or where at least one non-hydrocarbon atom or group has been inserted within the hydrocarbyl radical. Conveniently, each of $R^1$ and $R^2$ is independently selected from aliphatic alkoxy or aromatic alkoxy radicals, carboxy radicals, alkoxy-carbonyl radicals and hydrocarbon radicals, each of which radicals has 1 to 20 carbon atoms.

The present invention provides a process for oxidizing a hydrocarbon to the corresponding hydroperoxide, alcohol, ketone, carboxylic acid or dicarboxylic acid. The process comprises contacting a reaction medium comprising a hydrocarbon with an oxygen-containing gas in the presence of a catalyst comprising a cyclic imide of the general formula (I):

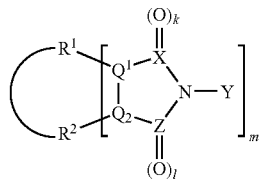

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I, provided that $R^1$ and $R^2$ can be linked to one another via a covalent bond; each of $Q^1$ and $Q^2$ is independently selected from C, CH, N, and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3; and $R^3$ can be any of the entities (radicals, groups, or atoms) listed for $R^1$. The contacting is conducted under conditions such as to maintain the concentration of water in the reaction medium below 50 ppm and the concentration of organic acids in the reaction medium below 50 ppm so that hydrolysis of the cyclic imide catalyst is minimized.

Preferably the weight concentration of water and organic acids other than target acids in the reaction medium is each independently maintained, by selection of process conditions, at 40 wppm or below, for example in the range 10 to 40 wppm such as 20 to 30 wppm.

As used herein, the numbering scheme for the Periodic Table Groups is employed as disclosed in Chemical and Engineering News, 63(5), 27 (1985).

Hydrocarbon Feed

Using the present process a wide group of substituted or unsubstituted saturated or unsaturated hydrocarbons, such as alkanes, cycloalkanes, alkenes, cycloalkenes, and aromatics, can be selectively oxidized. In particular, however, the process has utility in the selective oxidation of isobutane to tertiary butyl hydroperoxide and tertiary butanol, the selective oxidation of cyclohexane to cyclohexanol and cyclohexanone and the selective oxidation to the corresponding hydroperoxides of alkylaromatic compounds of the general formula (II):

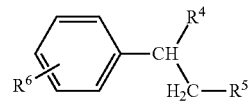

in which $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group. In an embodiment, $R^4$ and $R^5$ are joined to form a cyclic group having from 4 to 10 carbon atoms, conveniently a cyclohexyl group, substituted with one or more alkyl group having from 1 to 4 carbon atoms or with one or more phenyl groups. Examples of suitable alkylaromatic compounds are ethyl benzene, cumene, sec-butylbenzene, sec-pentylbenzene, p-methyl-sec-butylbenzene, 1,4-diphenylcyclohexane, sec-hexylbenzene, and cyclohexylbenzene, with cumene, sec-butylbenzene, cyclohexylbenzene and mixtures thereof being preferred.

In one practical embodiment, the alkylaromatic compound of general formula (II) is cumene and is produced by alkylating benzene with at least one $C_3$ alkylating agent, normally propylene, under alkylation conditions and in the presence of a heterogeneous catalyst, such as zeolite beta or more preferably at least one molecular sieve of the MCM-22 family (as defined below). The alkylation conditions conveniently include a temperature of from about 10° C. to about 250° C., for example between about 10° C. and about 150° C. The alkylation pressure is conveniently 25000 kPa or less, for example from about 100 to about 3000 kPa. The alkylation is conveniently carried out at a benzene to $C_3$ alkylating agent molar ratio of about 1 to about 10 and a weight hourly space velocity (WHSV) based on benzene of between about 5 and about 250 $hr^{-1}$, for example between about 5 and about 50 $hr^{-1}$.

In a further practical embodiment, the alkylaromatic compound of general formula (II) is sec-butylbenzene and is produced by alkylating benzene with at least one $C_4$ alkylating agent under alkylation conditions and in the presence of a heterogeneous catalyst, such as zeolite beta or more preferably at least one molecular sieve of the MCM-22 family (as defined below). The alkylation conditions conveniently include a temperature of from about 60° C. to about 260° C., for example between about 100° C. and about 200° C. The alkylation pressure is conveniently 7000 kPa or less, for example from about 1000 to about 3500 kPa. The alkylation is conveniently carried out at a molar ratio of benzene to $C_4$ alkylating agent of from about 1 to about 50, for example from about 2 to about 10, and a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

In yet a further practical embodiment, the alkylaromatic compound of general formula (II) is cyclohexylbenzene and is produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C. The contacting pressure may be, for example, from about 100 to about 7000 kPa. The benzene to hydrogen molar ratio in the contacting step is preferably from about 0.01 to about 100. The WHSV during the contacting step is preferably in the range of about 0.01 to about 100.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250, 277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

Hydrocarbon Oxidation

The oxidation step in the present process is effected by contacting the hydrocarbon substrate with an oxygen-containing gas, such as air, in the presence of a catalyst comprising a cyclic imide of the general formula (I):

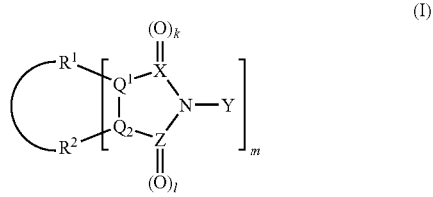

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I provided that (ie in certain embodiments) $R^1$ and $R^2$ may be linked to one another via a covalent bond; each of $Q^1$ and $Q^2$ is independently selected from C, CH, N, and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3, and $R^3$ can be any of the entities (radicals, groups, or atoms) listed for $R^1$. Conveniently, each of $R^1$ and $R^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

Generally, the cyclic imide employed as the oxidation catalyst obeys the general formula

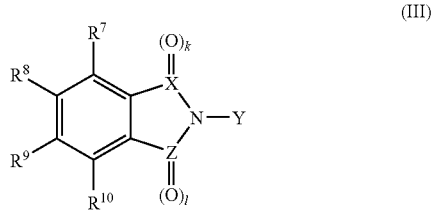

wherein each of $R^7$, $R^8$, $R^9$, and $R^{10}$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2. Conveniently, each of $R^7$, $R^8$, $R^9$, and $R^{10}$ is independently selected from aliphatic alkoxy or aromatic alkoxy radicals, carboxyl radicals, alkoxy-carbonyl radicals and hydrocarbon radicals, each of which radicals has 1 to 20 carbon atoms.

In one practical embodiment, the cyclic imide catalyst comprises N-hydroxyphthalimide (NHPI).

The contacting of the hydrocarbon substrate with an oxygen-containing gas in the presence of the cyclic imide catalyst is conducted under conditions that are effective not only to effect the desired oxidation of the substrate but also to maintain the concentration of both water and organic acids (e.g., acetic or formic acid) in the reaction medium below 50 ppm. Such conditions typically include conducting the oxidation at relatively low pressure, such as below 300 kPa, for example between about 50 kPa and about 200 kPa. Preferably the pressure is in the range of from 75 to 150 kPa, more preferably from 80 to 130 kPa.

Although the oxidation can be conducted over a broad oxygen concentration range such as between 0.1 and 100%, it is preferred to operate at relatively low oxygen concentration, such as no more than 21 volume %, for example from about 0.1 to about 21 volume %, generally from about 1 to about 10 volume %, oxygen in the oxygen-containing gas. The flow of oxygen-containing gas can be selected depending on the amount of feed (hydrocarbon substrate) present in the reaction vessel and the desired oxygen concentration.

In a preferred embodiment, maintaining the desired low levels of water and organic acids, is facilitated by passing a stripping gas through the reaction medium during the oxidation step. In one embodiment, the stripping gas is the same as the oxygen-containing gas and could, for example, be a recycle stream of spent oxygen-containing gas from the oxidation step. In another embodiment, the stripping gas is different from the oxygen-containing gas and is inert to the reaction medium and the cyclic imide catalyst. Suitable stripping gases include inert gases, such as helium and argon.

The temperature at which the oxidation reaction is performed is also a feature that to an extent determines the levels of water and organic acids in the reaction medium. Thus the contacting is conveniently carried out at a temperature of from 20° C. to 300° C., such as from 50° to 150° C. Preferably the temperature is maintained at a relatively high value, ie in excess of 100° C., such as in the range 105° C. to 130° C.

A further process condition that has been found to have an impact on water and organic acid concentration in the reaction medium is whether the medium is agitated, eg by stirring, during the oxidation reaction. Preferably stirring is carried out, for example with a stirrer operating in the range of from 500 to 1500 revolutions per minute (rpm), such as 600 to 1200 rpm, more preferably 700 to 1100 rpm. Without wishing to be bound by theory, it is believed that agitation, eg stirring, minimises the formation of regions in the reaction medium that have water, or organic acid concentrations of 50 ppm or more. Moreover, it has been found that agitation increases the oxygen concentration in the liquid phase, which in turn increases the rate of the oxidation reaction, since oxygen mass transfer (oxygen concentration in the liquid phase) is a limiting step in the oxidation reaction.

As will be understood, the applied oxidation conditions such as pressure, temperature, oxygen concentration, stripping and agitation (stirring) rate can be adjusted to suit the reaction components and catalyst employed. In accordance with the invention the conditions are selected such as to maintain the concentration of water in the reaction medium below 50 ppm and the concentration of organic acids in the reaction medium below 50 ppm.

An additional advantage of operating the oxidation process at low pressure and low oxygen concentration and by stripping water and organic acids, from the reaction medium is that light hydroperoxide (e.g., ethyl or methyl hydroperoxide), light ketones (e.g., methyl ethyl ketone), light aldehydes (e.g., acetaldehyde) and light alcohols (e.g., ethanol) are removed from the reaction products as they are formed. Thus light hydroperoxides are hazardous and pose a safety concern if their concentration in the liquid product becomes too high. Also, light hydroperoxides, alcohols, aldehydes and ketones are precursors for the formation of organic acids and water so that removing these species from the oxidation medium improves the oxidation reaction rate and selectivity and the stability of the cyclic imide catalyst. In fact, data show that when conducting oxidation of sec-butylbenzene with NHPI at 690 kPag (100 psig), more than 99 mol % of these light species and water remain in the reactor, whereas at atmospheric pressure, more than 95 mol % of these species are removed from the oxidation reactor.

Oxidation Product

The product of the present oxidation process depends on the nature of the hydrocarbon substrate being oxidized but in general is a hydroperoxide, alcohol, ketone, carboxylic acid or dicarboxylic acid, especially a hydroperoxide.

For example, when the hydrocarbon substrate is isobutane, the oxidation product comprises tertiary butyl hydroperoxide (which is useful as an oxidation reagent and in the production of propylene oxide) and tertiary butanol (which is useful as a gasoline additive).

When the hydrocarbon substrate is cyclohexane, the oxidation product comprises cyclohexyl hydroperoxide, cyclohexanol and cyclohexanone. Cyclohexyl hydroperoxide is readily decomposed to additional cyclohexanol and cyclohexanone, either thermally or with the assistance of a catalyst. Cyclohexanol can be oxidized with aqueous nitric acid to produce adipic acid, which is a precursor in the synthesis of Nylon 6,6, whereas cyclohexanone can be converted to cyclohexanoxime which undergoes acid-catalyzed rearrangement to produce caprolactam, a precursor in the synthesis of Nylon 6.

Where the hydrocarbon substrate is an alkylaromatic compound of the general formula (II), the product of the oxidation reaction includes a hydroperoxide of general formula (IV):

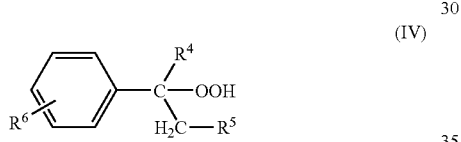

(IV)

in which $R^4$, $R^5$ and $R^6$ have the same meaning as in formula (II). Preferably, the hydroperoxide is sec-butylbenzene hydroperoxide, cumene hydroperoxide or cyclohexylbenzene hydroperoxide. This hydroperoxide can then be converted by acid cleavage to phenol or a substituted phenol and an aldehyde or ketone of the general formula $R^4COCH_2R^5$ (V), in which $R^4$ and $R^5$ have the same meaning as in formula (II).

The cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 1000 hr−1, preferably about 1 to about 50 hr−1. The hydroperoxide is preferably diluted in an organic solvent inert to the cleavage reaction, such as methyl ethyl ketone, phenol, cyclohexylbenzene, cyclohexanone or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

The crude product from the cleavage step may be purified to separate its components, or further treated to form further products. Thus in one embodiment where the compound (IV) is cyclohexylbenzenehydroperoxide, the ketone product will include cyclohexanone. Accordingly, the crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

Figure 21:
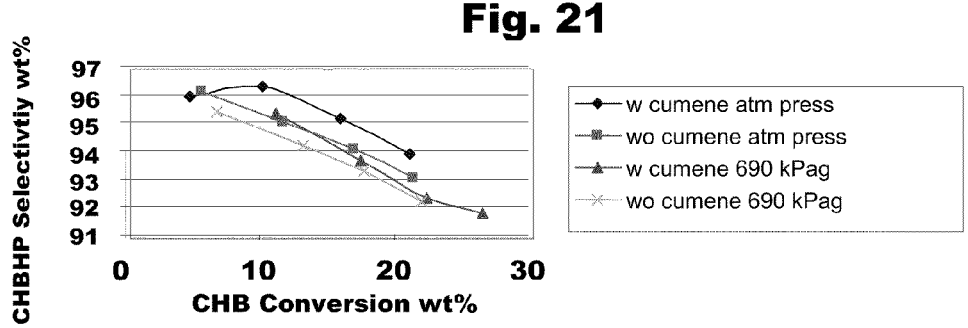
FIG. 21 is a graph plotting cyclohexylbenzene hydroperoxide (CHBHP) selectivity against cyclohexylbenzene (CHB) conversion in the oxidation of a mixture of CHB and cumene at 100 kPa (atmospheric pressure) and at 690 kPag (100 psig) in the initial presence of 0.1 wt % (1000 ppm) NHPI according to the process of Example 12 (ie Examples 12A and 12B).
Figure 22:
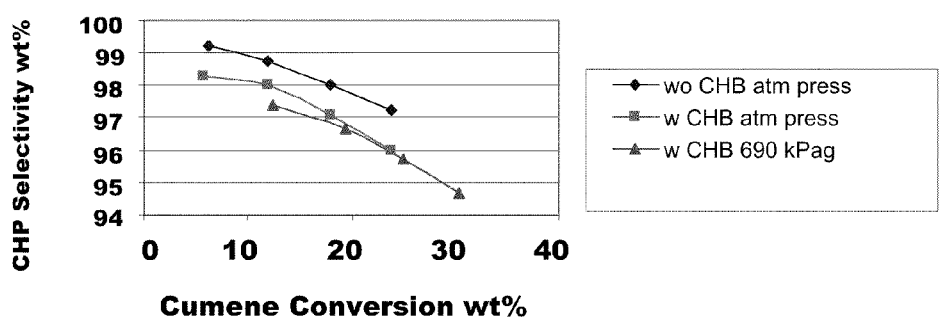
FIG. 22 is a graph plotting cumene hydroperoxide (CHP) selectivity against cumene conversion in the oxidation of a mixture of CHB and cumene at 100 kPa (atmospheric pressure) and at 690 kPag (100 psig) in the initial presence of 0.1 wt % (1000 ppm) NHPI according to the process of Example 12.
Figure 23:
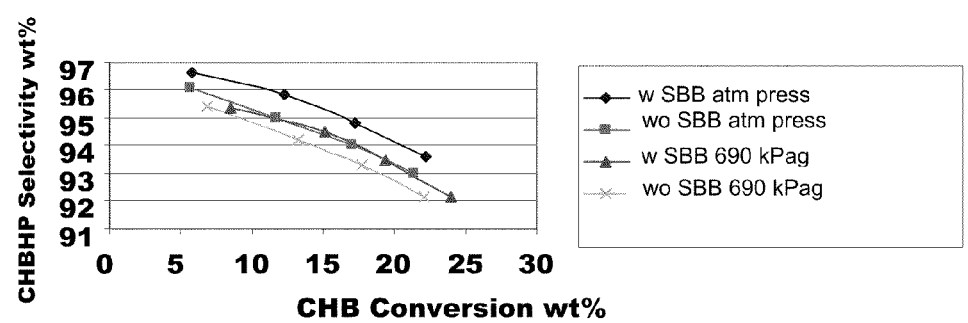
FIG. 23 is a graph plotting cyclohexylbenzene hydroperoxide (CHBHP) selectivity against cyclohexylbenzene (CHB) conversion in the oxidation of a mixture of CHB and se-butylbenzene (SBB) at 100 kPa (atmospheric pressure) and at 690 kPag (100 psig) in the initial presence of 0.1 wt % (1000 ppm) NHPI according to the process of Example 13 (ie Examples 13A and 13B).

In one embodiment of the invention, the hydrocarbon substrate that is oxidized is a mixture of two compounds of general formula (II). In certain cases a synergystic effect has been identified when co-feeding mixed feeds to contact with the specified catalyst under the specified oxidation process conditions. Such synergy is seen, for example, when the hydrocarbon substrate is a mixture of cumene and cyclohexylbenzene; or a mixture of sec-butylbenzene and cyclohexylbenzene. This synergystic effect is demonstrated in Examples 12 and 13 and their associated FIGS. 21-23 discussed hereinafter.

The invention will now be more particularly described with reference to the following non-limiting Examples, some of the data from which are shown in Table 1.

Example 1

Oxidation of SBB 150 gm of sec-butylbenzene (SBB) supplied by TCI America and 0.16 gm (0.11 wt %, 1100 ppm) of N-hydroxyphthalimide (NHPI) were weighed into a Parr reactor fitted with a stirrer, thermocouple, gas inlet, sampling port and a condenser containing a Dean Stark trap for water removal. The reactor and contents were stirred at 700 rpm and sparged with nitrogen at a flow rate of 250 cc/minute for 5 minutes. The reactor was then pressurized with nitrogen to 690 kPag (100 psig) while maintained under a nitrogen sparge and was then heated to 125° C. When the reaction temperature was reached, the gas was switched from nitrogen to air and the reactor was sparged with air at 250 cc/minute for 4 hours. Samples were taken hourly and the NHPI, acetic acid and reactant concentrations of each sample were measured by gas chromatography for conversion and selectivity and HPLC (High Pressure Liquid Chromatography) for NHPI concentration measurements. For water analysis Karl Fischer analysis was used. After 4 hours, the gas was switched back to nitrogen and the heat was turned off. When the reactor had cooled, it was depressurized and the contents removed.

The results are shown in Table 1 and in FIG. 1, from which it will be seen that the NHPI concentration dropped from 1100 wppm at the beginning of the test to 185 wppm over 4 hours, during which time the acetic acid concentration built up from zero to about 600 wppm. Over the same time the ethyl hydroperoxide concentration built up to about 2000 wppm and the water concentration to be in excess of 1000 wppm.

Example 2

Oxidation of SBB

Figure 2:
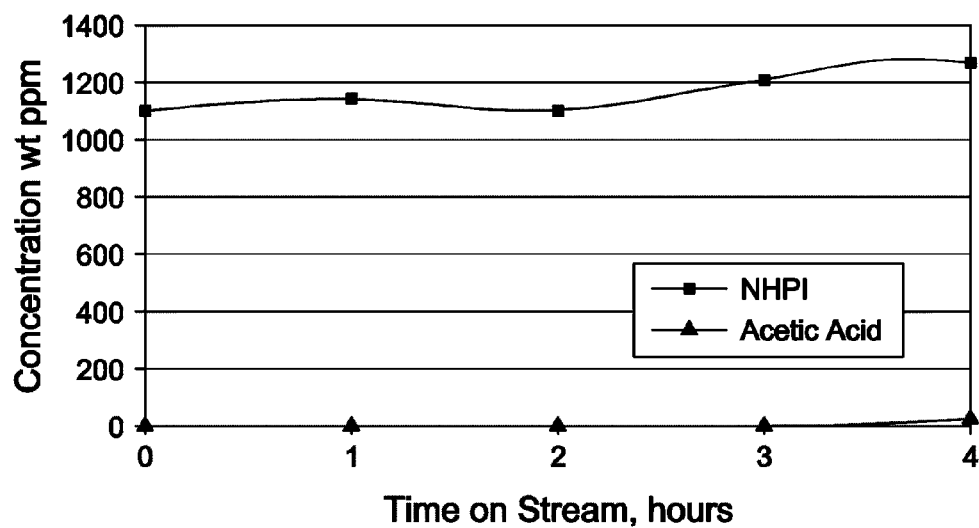
FIG. 2 is a graph plotting acetic acid and NHPI concentration against time on stream in the oxidation of SBB in the initial presence of 0.11 wt % (1100 ppm) NHPI at 100 kPa (atmospheric pressure) according to the process of Example 2.

The process of Example 1 was repeated but with the test being run at atmospheric pressure (100 kPa) and the results are shown in Table 1 and in FIG. 2. It will be seen that, at atmospheric pressure (100 kPa), acetic acid and other light acids were formed at very low concentration and were completely removed from the reaction mixture, making them unavailable to catalyze the hydrolysis of the NHPI. In fact for the first 3 hours of the test, the acetic acid and the ethyl hydroperoxide levels were below the detection limits of the gas chromatographic analysis, rising to only 30 and 34 ppm for acetic acid and ethyl hydroperoxide respectively (in contrast with the 600 and 2000 ppm obtained in Example 1), by the end of the 4 hour run time. In addition to stripping acetic acid from the reaction mixture, at low pressure the air flowing through the reactor stripped out the majority of the water also generated as a by-product of the oxidation process, to a level below 50 wppm.

The NHPI concentration during the test of Example 2 is also shown in FIG. 2, from which it will be seen that the concentration of NHPI started out at 1100 ppm and drifted up slowly during the test as other volatile components were stripped from the reaction mixture. Thus, at low pressure, with most of the acetic acid and water removed to levels below 50 wppm, the NHPI catalyst in the reaction vessel was protected from hydrolysis and remained close to its starting concentration and available for the oxidation reaction.

Figure 3:
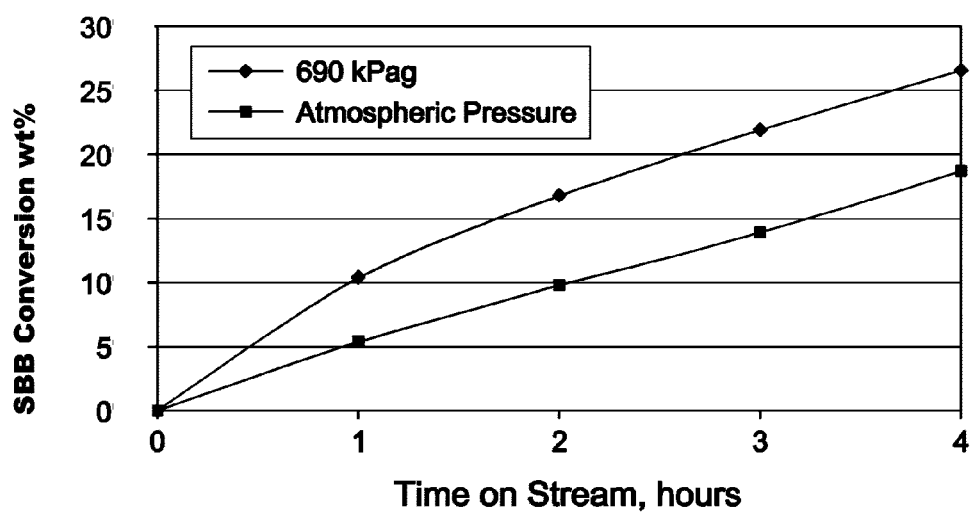
FIG. 3 is a graph comparing the SBB conversion (wt %) against time on stream for the processes of Examples 1 and 2.
Figure 4:
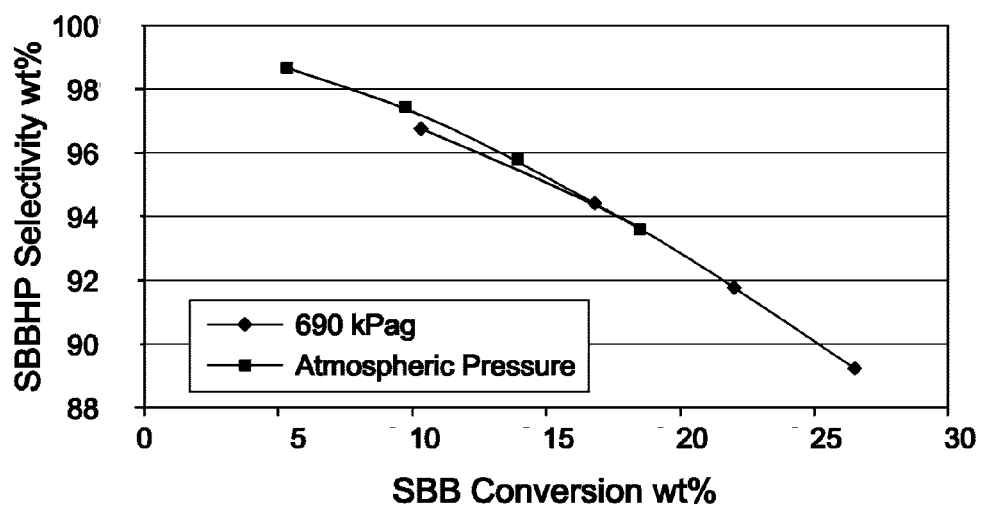
FIG. 4 is a graph comparing the sec-butylbenzene hydroperoxide (SBBHP) selectivity (wt %) against SBB conversion (wt %) for the processes of Examples 1 and 2.

The SBB conversion and the selectivity to sec-butylbenzene hydroperoxide (SBBHP) for Examples 1 and 2 are compared in FIGS. 3 and 4. It will be seen from FIG. 3 that the SBB conversion was adversely affected by the lower pressure used in Example 2, being 26 wt % after 4 hours in Example 1 but only 18 wt % in Example 2. However, as can be seen from FIG. 4, the SBBHP selectivity versus SBB conversion response was very similar at both 690 kPag (100 psig) and atmospheric pressure, indicating that the SBBHP selectivity was set by the SBB conversion selected and was not a function of pressure at these reaction conditions.

Examples 3 and 4

Oxidation of SBB

Figure 5:
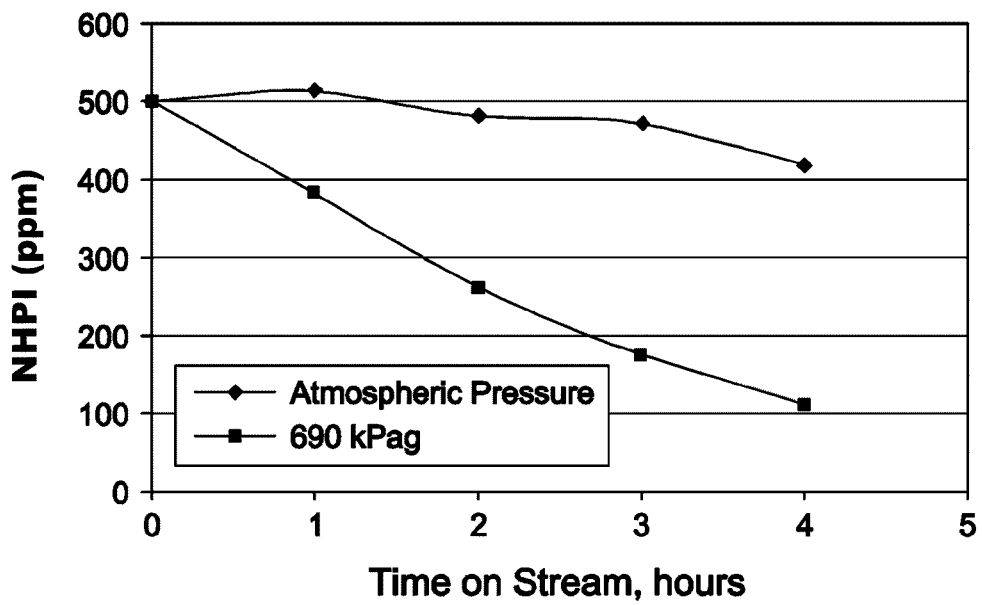
FIG. 5 is a graph plotting NHPI concentration (wt ppm) against time on stream in the oxidation of SBB in the initial presence of 0.05 wt % (500 ppm) NHPI at 690 kPag (100 psig) according to the process of Example 3 and at 100 kPa (atmospheric pressure) according to the process of Example 4.
Figure 6:
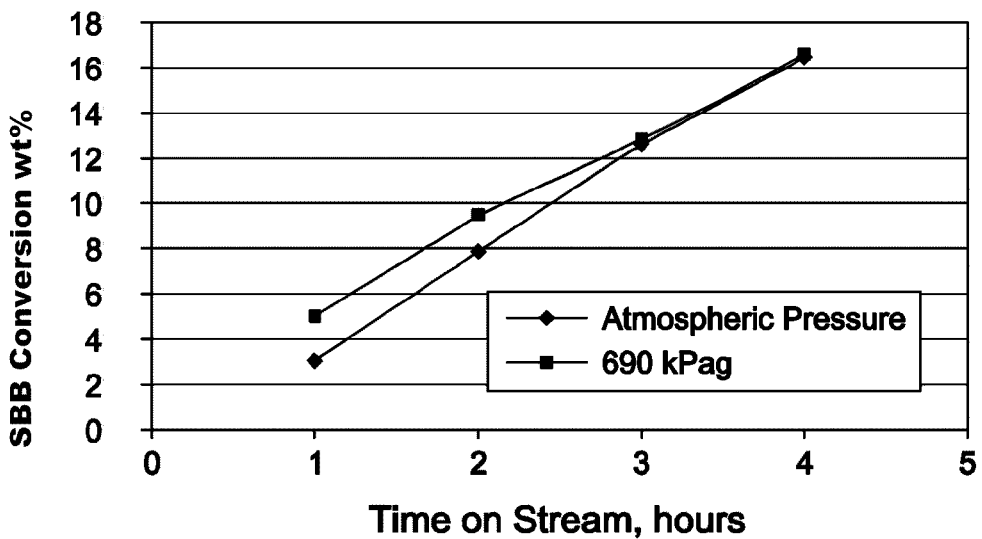
FIG. 6 is a graph plotting SBB conversion (wt %) against time on stream in the oxidation of SBB in the initial presence of 0.05 wt % (500 ppm) NHPI at 690 kPag (100 psig) according to the process of Example 3 and at 100 kPa (atmospheric pressure) according to the process of Example 4.
Figure 7:
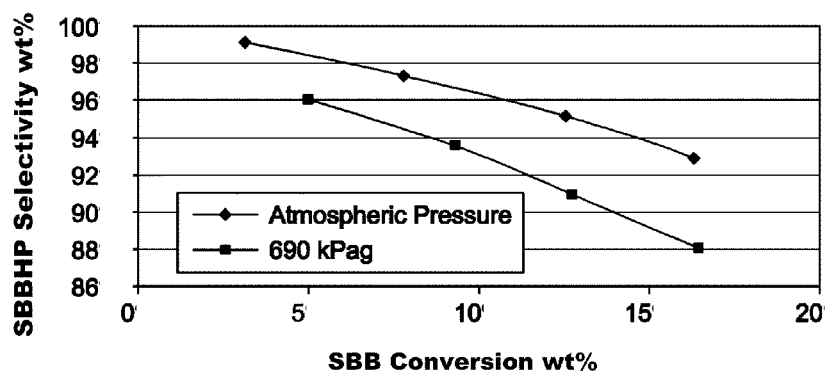
FIG. 7 is a graph plotting SBBHP selectivity (wt %) against SBB conversion (wt %) in the oxidation of SBB in the presence of 0.05 wt % (500 ppm) NHPI at 690 kPag (100 psig) according to the process of Example 3 and at 100 kPa (atmospheric pressure) according to the process of Example 4.

The processes of Examples 1 and 2 were repeated but with the initial NHPI concentration being decreased to 0.05 wt % (500 ppm) and the results are shown in Table 1 and in FIGS. 5 to 7.

FIG. 5 plots the NHPI concentration against time on stream and shows that the concentration dropped from 500 ppm to 100 ppm over the 4 hours of the test at 690 kPag (100 psig) in Example 3, but only dropped to 420 ppm over 4 hours at atmospheric pressure (100 kPa) in Example 4. The water and organic acid measurements for the conditions of Example 3 after 4 hours were >1000 and >500 wppm respectively; whereas for Example 4 they were each <50 wppm.

FIG. 6 plots the SBB conversion against time on stream and shows that the conversion in both Examples 3 and 4 was essentially the same at about 17 wt % after the 4 hours of the test.

FIG. 7 plots the SBBHP selectivity against the SBB conversion and shows that the SBBHP selectivity was significantly better at atmospheric pressure (100 kPa) than at 690 kPag (100 psig) over the entire range of SBB conversions tested.

Examples 5A, 5B and 5C

Oxidation of SBB

As shown in FIG. 3, the SBB conversion in Example 2 was adversely affected by the lower pressure employed, indicating that oxygen mass transfer (oxygen concentration in the liquid phase) is the limiting step in the oxidation reaction. One approach for improving the oxygen concentration in the liquid phase is to increase the rate of agitation of the reaction medium, by increasing the agitation speed of a stirrer in contact with the reaction medium. Thus in Example 5, the effect of stirrer agitation speed was evaluated at different pressures, namely at 690 kPag (100 psig), 207 kPag (30 psig) and atmospheric pressure (100 kPa) in Examples 5A, 5B and 5C respectively. In particular, the process of Example 1 was repeated but with the reactor and contents being stirred at various rates between 0 and 1500 rpm at each of the pressures tested. The results are summarized in Table 1 and in FIGS. 8 to 11.

Figure 8:
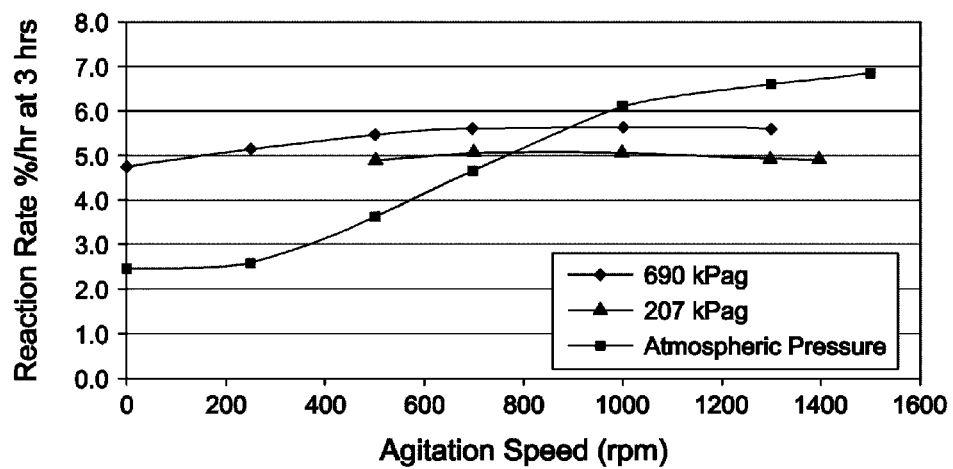
FIG. 8 is a graph plotting the reaction rate (wt % per hour) against stirrer agitation speed at different pressures in the oxidation of sec-butylbenzene (SBB) in the presence of 0.1 wt % (1000 ppm) NHPI according to the process of Example 5 (ie Examples 5A, 5B and 5C).
Figure 9:
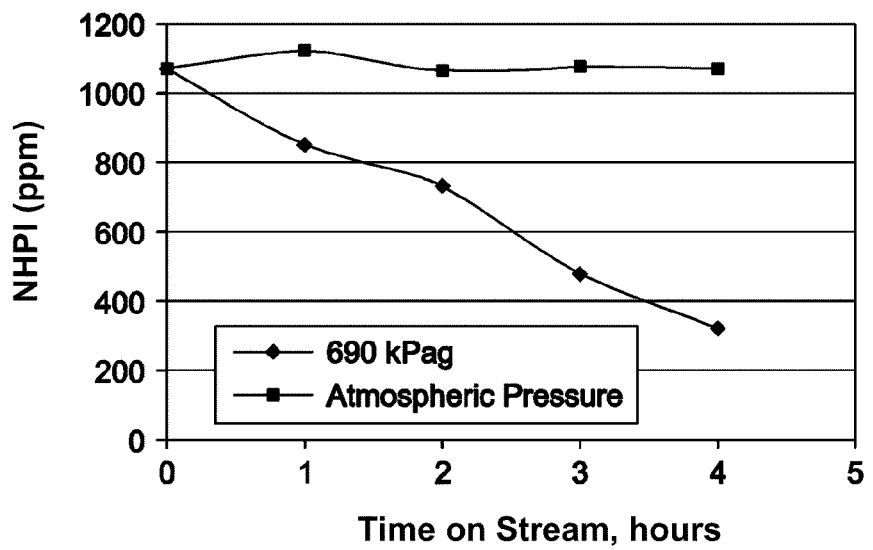
FIG. 9 is a graph plotting NHPI concentration against time on stream in the oxidation of sec-butylbenzene (SBB) at 100 kPa (atmospheric pressure) and at 690 kPag (100 psig) in the presence of 0.1 wt % (1000 ppm) NHPI and with the reaction medium being agitated by a stirrer rotating at 1000 rpm according to the process of Example 5.

FIG. 8 plots the reaction rate (wt %) against agitation speed at different pressures and shows that the reaction rate at high pressure, 207 kPag and 690 kPag (30 and 100 psig), is almost not affected by the agitation speed. However, at atmospheric pressure, the reaction rate is dramatically affected by the agitation speed. This is believed to be because undesirable product mixture components (water and organic acid, especially low molecular weight organic acid such as acetic acid) are removed to levels below 50 wppm at atmospheric pressure and the NHPI stability is improved (FIG. 9). At the same time the oxygen concentration in the liquid phase is increased by the high speed agitation. The measured values for water, organic acid and NHPI catalyst concentrations under the different process conditions are shown in Table 1.

Figure 10:
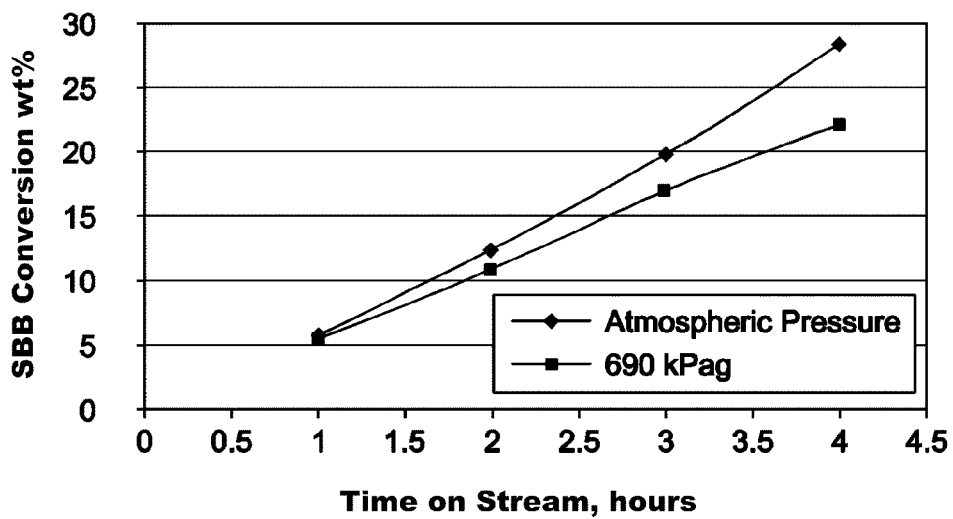
FIG. 10 is a graph plotting SBB conversion against time on stream in the oxidation of sec-butylbenzene (SBB) at 100 kPa (atmospheric pressure) and at 690 kPag (100 psig) in the presence of 0.1 wt % (1000 ppm) NHPI and with the reaction medium being agitated by a stirrer rotating at 1300 rpm according to the process of Example 5.
Figure 11:
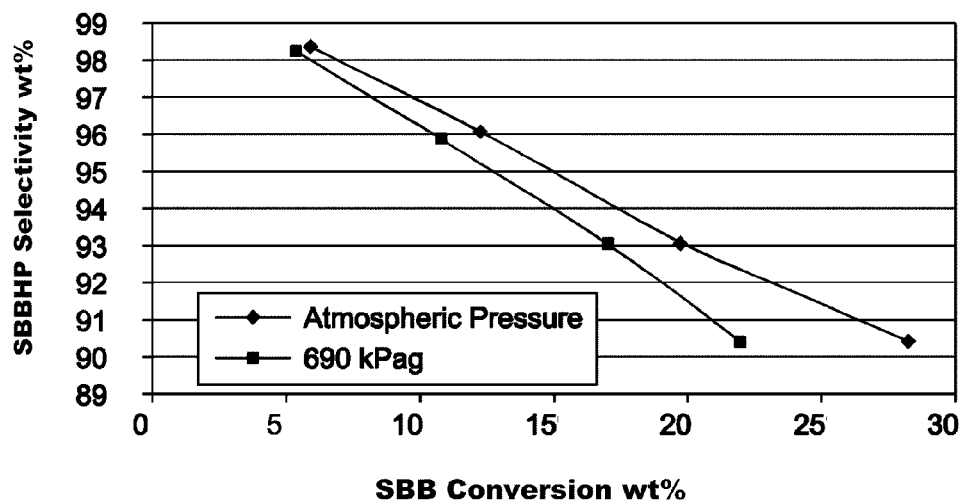
FIG. 11 is a graph plotting SBBHP selectivity against SBB conversion in the oxidation of sec-butylbenzene (SBB) at 100 kPa (atmospheric pressure) and at 690 kPa (100 psig) in the initial presence of 0.1 wt % (1000 ppm) NHPI and with the reaction medium being agitated by a stirrer rotating at 1300 rpm according to the process of Example 5.

FIGS. 10 and 11 show that, at high speed agitation and atmospheric pressure, not only is the NHPI stability improved but also the SBB conversion and SBBHP selectivity are increased.

Example 6

Oxidation of CHB

The process of Example 1 was repeated but with the test being run with 150 gm of cyclohexylbenzene (CHB) supplied by TCI America and 0.16 gm (0.11 wt %, 1100 wppm) of N-hydroxyphthalimide (NHPI) being weighed into a Parr reactor fitted with a stirrer, thermocouple, gas inlet, sampling port and a condenser containing a Dean Stark trap for water removal. The reactor and contents were stirred at 1000 rpm and sparged with nitrogen at a flow rate of 250 cc/minute for 5 minutes. The reactor was then pressurized with nitrogen to 690 kPag (100 psig) while maintained under a nitrogen sparge and was then heated to 115° C. When the reaction temperature was reached, the gas was switched from nitrogen to air and the reactor was sparged with air at 250 cc/minute for 4 hours. Samples were taken hourly and the NHPI and the reaction component concentrations of each sample were measured by gas chromatography for conversion and selectivities and HPLC (High Pressure Liquid Chromatography) for NHPI concentration measurements. After 4 hours, the gas was switched back to nitrogen and the heat was turned off. When the reactor had cooled, it was depressurized and the contents removed. The results are shown in Table 1 and in FIGS. 12, 13 and 14. Product analyses showed inter alia that some amounts of benzoic acid and pentanioc acid had been formed.

Example 7

Oxidation of CHB

Figure 12:
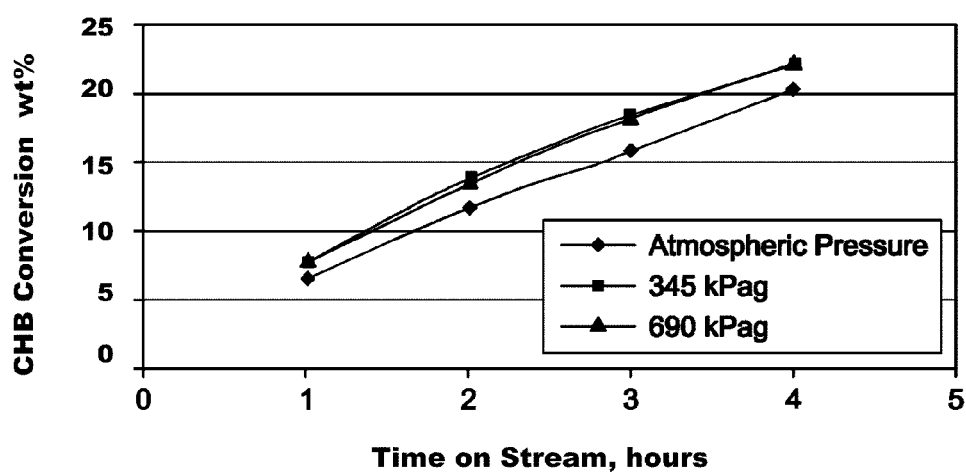
FIG. 12 is a graph plotting the conversion of cyclohexylbenzene (CHB) against time on stream in the oxidation of CHB in the initial presence of 0.1 wt % (1000 ppm) NHPI at 100 kPa (atmospheric pressure), 345 kPag (50 psig) and 690 kPag (100 psig) and with stirring at 1000 rpm according to the process of Examples 6 to 8.
Figure 13:
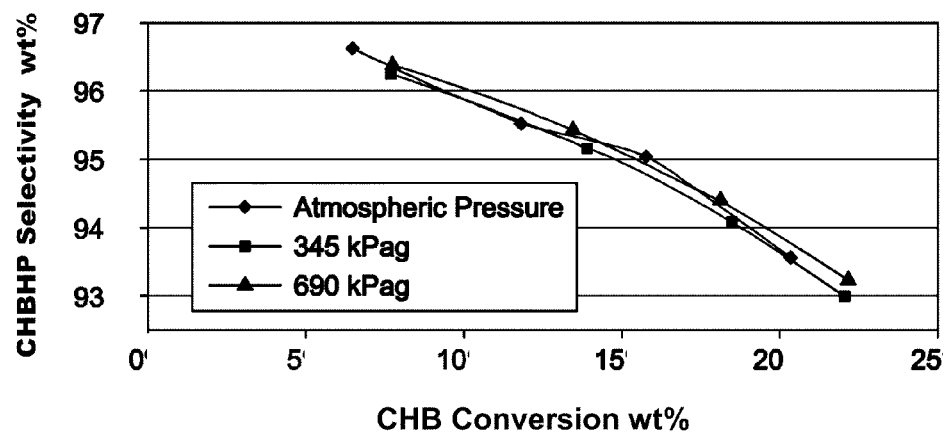
FIG. 13 is a graph comparing cyclohexylbenzene hydroperoxide (CHBHP) selectivity against CHB conversion for the processes of Examples 6 to 8.
Figure 14:
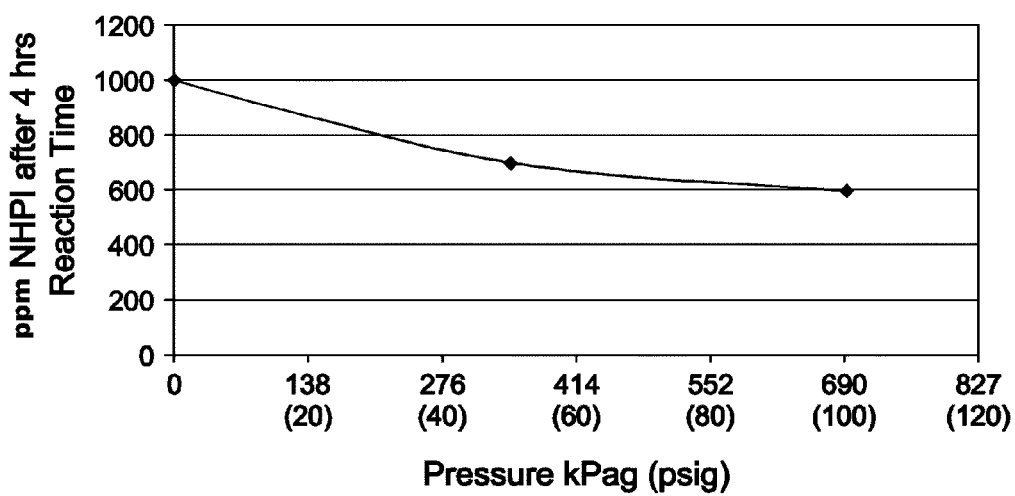
FIG. 14 is a graph plotting NHPI concentration against pressure after 4 hours reaction time in the oxidation of CHB according to the processes of Examples 6 to 8.

The process of Example 6 was repeated but with the test being run at a pressure of 345 kPag (50 psig). Again the results are shown in FIGS. 12, 13 and 14.

Example 8

Oxidation of CHB

The process of Example 6 was repeated but with the test being run at atmospheric pressure (100 kPa or 0 kPag). Again the results are shown in FIGS. 12, 13 and 14. It will be seen from FIGS. 12, 13 and 14 that the CHB conversion and the selectivity to the hydroperoxide were not affected by the pressure decrease between Examples 6 to 8. However, the NHPI concentration was affected by the pressure employed in the test. Thus, at atmospheric pressure, the NHPI concentration remained substantially the same over the 4 hours of the test, but at 345 and 690 kPag (50 and 100 psig) the NHPI concentration dropped from 1100 ppm at the beginning of the test to 700 and 600 ppm respectively at the end of the test. The water and organic acid concentration values for Examples 6-8 are shown in Table 1.

Example 9

Oxidation of CHB

Figure 15:
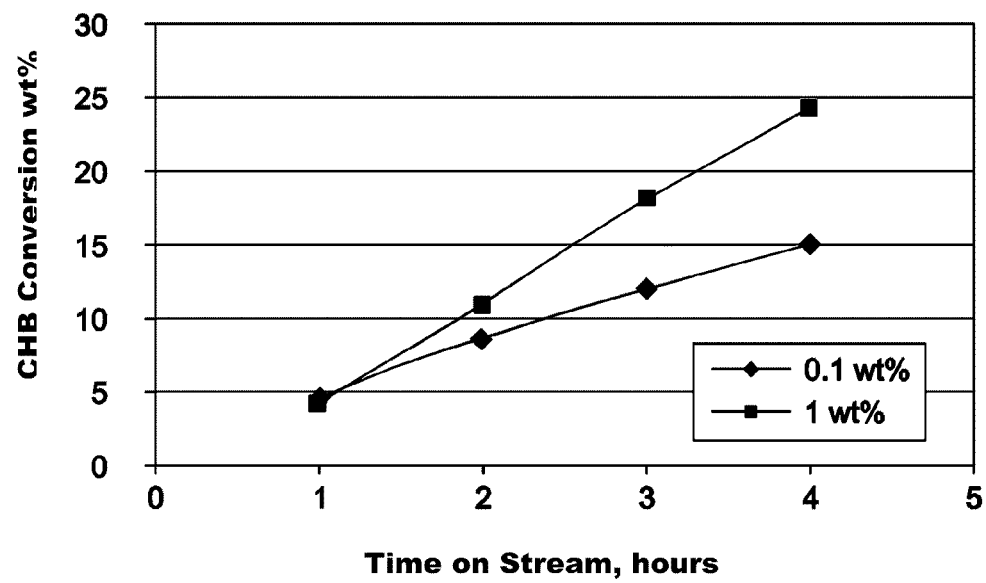
FIG. 15 is a graph plotting CHB conversion against time on stream in the oxidation of cyclohexylbenzene (CHB) at 100 kPa (atmospheric pressure) in the initial presence of 0.1 wt % (1000 ppm) and 1 wt % (10 000 ppm) NHPI according to the processes of Examples 6 and 9.
Figure 16:
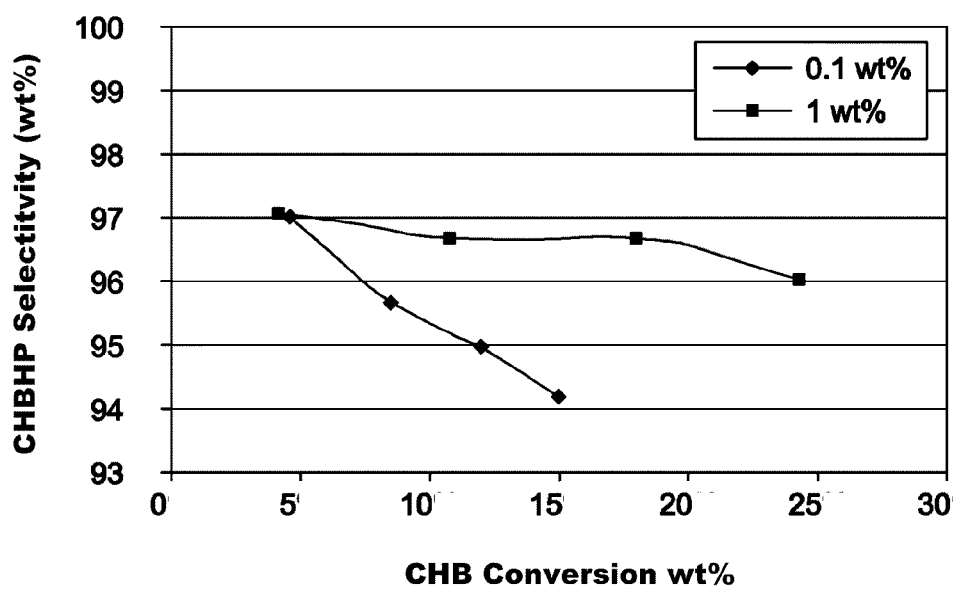
FIG. 16 is a graph plotting CHBHP selectivity against CHB conversion in the oxidation of cyclohexylbenzene (CHB) at 100 kPa (atmospheric pressure) in the initial presence of 0.1 wt % (1000 ppm) and 1 wt % (10 000 ppm) NHPI according to the processes of Examples 6 and 9.

The process of Example 6 was repeated but with the test being run with 1 wt % (10000 ppm) NHPI at atmospheric pressure and at 110° C. The results are shown in Table 1 and in FIGS. 15 and 16, from which it will be seen that the conversion and selectivity were dramatically improved by the presence of 1 wt % NHPI. In addition, the NHPI concentration remained the same, with no NHPI decomposition being observed using HPLC analysis.

Examples 10A and 10B

Oxidation of Cumene

Figure 17:
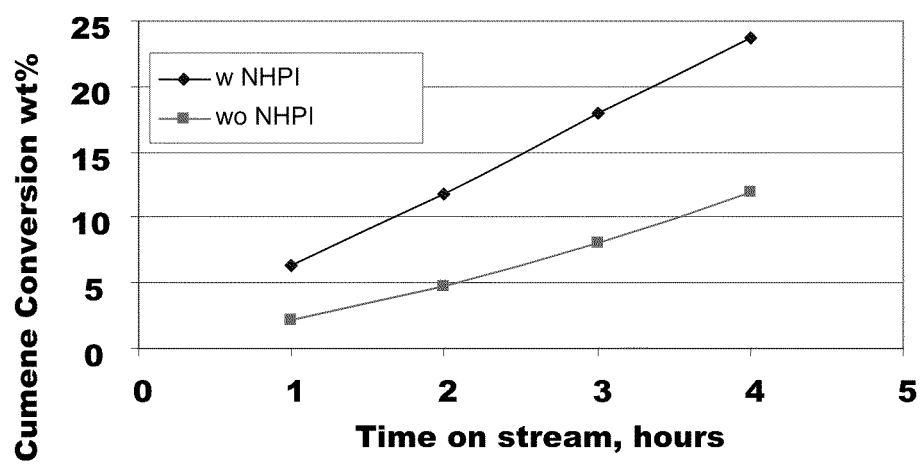
FIG. 17 is a graph plotting cumene conversion against time on stream in the oxidation of cumene at 100 kPa (atmospheric pressure) both with an initial presence of 0.11 wt % (1100 ppm) NHPI and without any NHPI, according to the process of Example 10 (ie Examples 10A and 10B).
Figure 18:
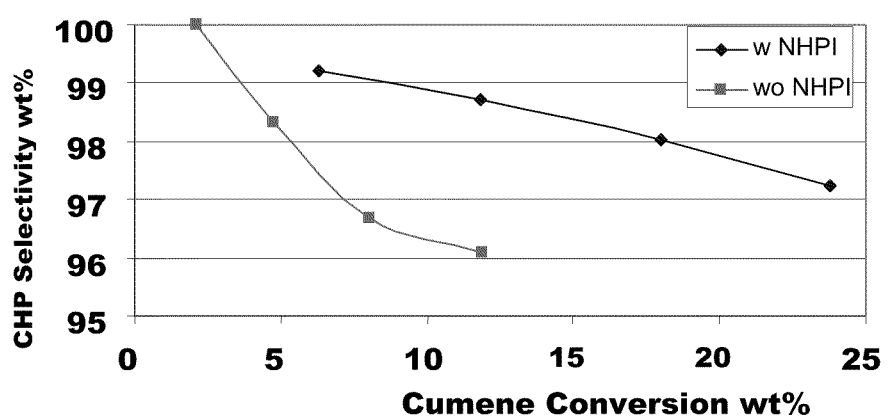
FIG. 18 is a graph plotting cumene hydroperoxide (CHP) selectivity against cumene conversion in the oxidation of cumene at 100 kPa (atmospheric pressure) both with an initial presence of 0.11 wt % (1100 ppm) NHPI and without any NHPI, according to the process of Example 10.

In this experiment 150 grams of cumene as supplied by TCI America and 0.16 grams (0.11 wt %, 1100 ppm) of NHPI were placed in an autoclave, heated to 115° C. and oxidized in a semi-batch process by introducing a 250 cc/min air flow for four hours at atmospheric pressure (100 kPa). Samples of the reactor contents were taken every hour. The process was repeated without the addition of NHPI (Example 10B) and the results are shown in Table 1 and in FIGS. 17 and 18. It will be seen that the addition of 0.11 wt % NHPI dramatically improved the cumene conversion and selectivity.

Examples 11A and 11B

Oxidation of Cumene

Figure 19:
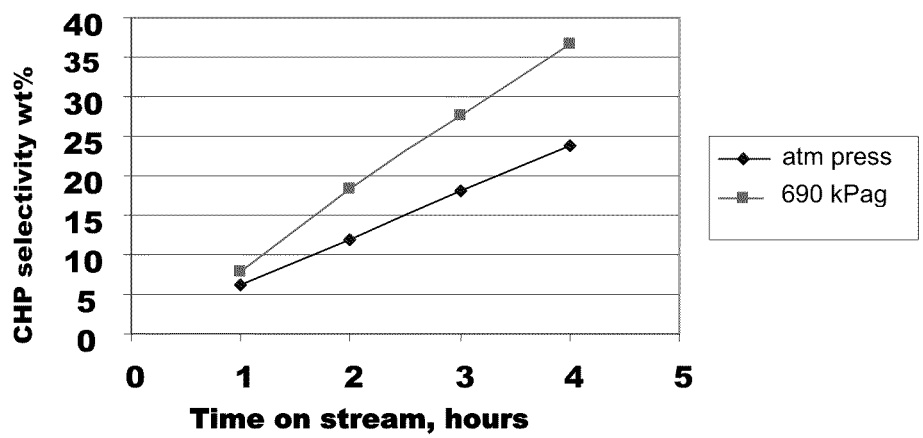
FIG. 19 is a graph plotting cumene hydroperoxide (CHP) selectivity against time on stream in the oxidation of cumene at 100 kPa (atmospheric pressure) and at 690 kPag (100 psig) in the initial presence of 0.1 wt % (1000 ppm) NHPI according to the process of Example 11 (ie Examples 11A and 11B).
Figure 20:
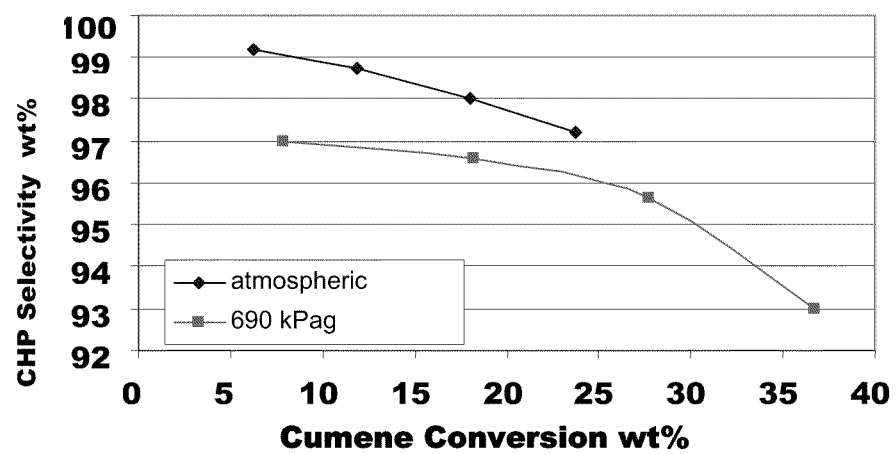
FIG. 20 is a graph plotting cumene hydroperoxide (CHP) selectivity against cumene conversion in the oxidation of cumene at 100 kPa (atmospheric pressure) and at 690 kPag (100 psig) in the initial presence of 0.1 wt % (1000 ppm) NHPI according to the process of Example 11.

The process of Example 10 was repeated but using an initial concentration of 0.11 wt % (1100 ppm) of NHPI as a catalyst and with separate runs being conducted at atmospheric pressure (100 kPa) and a pressure of 690 kPag (100 psig). The results are shown in Table 1 and in FIGS. 19 and 20, from which it will be seen that, although increasing the pressure improves the reaction rate (FIG. 19), it negatively affects the selectivity (FIG. 20). Generally, improving the hydroperoxide selectivity is more important than improving the conversion since side-reactions complicate product separation and cause phenol yield loss. Analysis of the products of the two runs shows the following:

(a) The NHPI remains intact (measured value 1081 ppm) at atmospheric pressure but at 690 kPag (100 psig) the NHPI concentration dropped from a measured value of 1060 ppm to 286 ppm at the end of the reaction.

(b) At atmospheric pressure most of the oxygenated products made from methyl radical oxidation are removed from the reactor (hence acid-concentration<50 ppm). However at 690 kPag (100 psig) most of the light oxygenates remain in the reactor (acid concentration>500 ppm) causing damage to the catalyst and the desired product. Also at the high pressure, the water concentration was measured at >1000 ppm.

(c) The concentration of phenol (made from hydroperoxide cleavage) in the oxidation effluent is found to be high (5000 ppm) at high pressure. At atmospheric pressure the phenol concentration is negligible.

Examples 12A and 12B

Oxidation of CHB/Cumene

A mixture of 116 grams of cyclohexylbenzene (CHB), 36 grams of cumene and 0.1 wt % (1000 ppm) of NHPI were weighed into a 300 ml Parr Reactor fitted with a stirrer, thermocouple, gas inlet, sampling port and a condenser containing a Dean Stark Trap for water removal. The reactor and contents were stirred at 1000 rpm and sparged with nitrogen at a flow rate of 250 cc/min for five minutes. The reactor was pressurized with nitrogen to the desired pressure (atmospheric or 690 kPag [100 psig]) and while maintaining a nitrogen sparge the reactor was heated to the desired temperature (115° C.). When the reaction temperature was reached, the gas was switched from nitrogen to air and the reactor was sparged with air at the desired flow rate for four hours. Samples were taken hourly. After four hours the gas was switched back to nitrogen and the heat was turned off. When the reactor had cooled, the reactor was depressurized and the contents removed. The results are shown in Table 1 and in FIGS. 21 and 22. The data show a synergistic effect when a mixture of CHB and cumene is oxidized and that the selectivity to the hydroperoxide is better at atmospheric pressure than at high pressure. Also, at 690 kPag the water and organic acid concentration was >1000 and >500 ppm, respectively.

Examples 13A and 13B

Oxidation of CHB/SBB

A mixture of 116 grams of cyclohexylbenzene (CHB), 36 grams of sec-butylbenzene and 0.1 wt % (1000 ppm) of NHPI were weighed into a 300 ml Parr Reactor fitted with a stirrer, thermocouple, gas inlet, sampling port and a condenser containing a Dean Stark Trap for water removal. The reactor and contents were stirred at 1000 rpm and sparged with nitrogen at a flow rate of 250 cc/min for five minutes. The reactor was pressurized with nitrogen to the desired pressure (atmospheric or 690 kPag [100 psig]) and while maintaining a nitrogen sparge the reactor was heated to the desired temperature (125° C.). When the reaction temperature was reached, the gas was switched from nitrogen to air and the reactor was sparged with air at the desired flow rate for four hours. Samples were taken hourly. After four hours the gas was switched back to nitrogen and the heat was turned off. When the reactor had cooled the reactor was depressurized and the contents removed. The results are shown in Table 1 and in FIG. 23. The data show a synergistic effect when a mixture of CHB and sec-butylbenzene is oxidized and that the selectivity to the hydroperoxide is better at atmospheric pressure (when water and organic acid were both <50 ppm) than at high pressure (when water was >1000 ppm and organic acid was >500 ppm).

The data reported in the Examples are at least in part listed in Table 1, where the units and abbreviations employed in the columns are: Water=wppm; Acid=wppm; Air=flow rate in cc/minute; Stirrer=stirring speed in revolutions per minute (rpm); temperature (T)=° C.; pressure (P)=kPa guage [the value zero indicates atmospheric pressure ie 100 kPa absolute]; NHPI=amount of catalyst in wppm; TOS=time on stream, in hours; and "Invention" indicates whether the Example is within the invention as claimed ("Yes") or not ("No").

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

TABLE 1

| Example | Feed | Water | Acid | Air | Stirrer | T | P | NHPI | TOS | Invention |
|---|---|---|---|---|---|---|---|---|---|---|
| 1 | SBB | >1000 | 0 → 600 | 250 | 700 | 125 | 690 | 1100 → 185 | 4 | No |
| 2 | SBB | <50 | 0 → 30 | 250 | 700 | 125 | 0 | 1100 → 1200 | 4 | Yes |
| 3 | SBB | >1000 | >500 | 250 | 700 | 125 | 690 | 500 → 100 | 4 | No |
| 4 | SBB | <50 | <50 | 250 | 700 | 125 | 0 | 500 → 420 | 4 | yes |
| 5A | SBB | >1000 | >500 | 250 | 0 → 1500 | 125 | 690 | 1100 → (200-250) | 4 | No |
| 5B | SBB | >500 | >300 | 250 | 0 → 1500 | 125 | 207 | 1100 → (450-500) | 4 | No |
| 5C | SBB | <50 | <50 | 250 | 0 → 1500 | 125 | 0 | 1100 → (1100-1000) | 4 | Yes |
| 6 | CHB | >1000 | >500 | 250 | 1000 | 115 | 690 | 1100 → 700 | 4 | No |
| 7 | CHB | >500 | >250 | 250 | 1000 | 115 | 345 | 1100 → 600 | 4 | No |
| 8 | CHB | <50 | <50 | 250 | 1000 | 115 | 0 | 1100 → 1100 | 4 | Yes |
| 9 | CHB | <50 | <50 | 250 | 1000 | 110 | 0 | 10000 → 10000 | 4 | Yes |
| 10A | Cumene | <50 | <50 | 250 | 1000 | 115 | 0 | 1100 → (1100-1000) | 4 | Yes |
| 10B | Cumene | >50 | <50 | 250 | 1000 | 115 | 0 | 0 | 4 | No |
| 11A | Cumene | <50 | <50 | 250 | 1000 | 115 | 0 | 1100 → 1081 | 4 | Yes |
| 11B | Cumene | >1000 | >500 | 250 | 1000 | 115 | 690 | 1100 → 286 | 4 | No |
| 12A | CHB/Cumene | <50 | <50 | 250 | 1000 | 115 | 0 | 1100 → (1100-1000) | 4 | Yes |
| 12B | CHB/Cumene | >1000 | >500 | 250 | 1000 | 115 | 690 | 1100 → <500 | 4 | No |
| 13A | CHB/SBB | <50 | <50 | 250 | 1000 | 125 | 0 | 1100 → (1100-1000) | 4 | Yes |
| 13B | CHB/SBB | >1000 | >500 | 250 | 1000 | 125 | 690 | 1100 → <200 | 4 | No |

The invention claimed is:

1. A process for oxidizing cyclohexylbenzene to produce a hydroperoxide thereof, the process comprising contacting a reaction medium comprising cyclohexylbenzene with an oxygen-containing gas in the presence of a catalyst comprising a cyclic imide of the general formula (I):

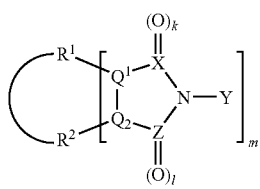

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$ or from the atoms H, F, Cl, Br and I, provided that $R^1$ and $R^2$ can be linked to one another via a covalent bond;

each of $Q^1$ and $Q^2$ is independently selected from C, CH, N, and $CR^3$;

each of X and Z is independently selected from C, S, $CH_2$, N, P and elements of Group 4 of the Periodic Table;

Y is O or OH;

k is 0, 1, or 2;

l is 0, 1, or 2;

m is 1 to 3; and $R^3$ can be any of the entities listed for $R^1$; and wherein said contacting is conducted under conditions such as to maintain the concentration of water in the reaction medium below 50 ppm by weight and the concentration of organic acids in the reaction medium below 50 ppm by weight.

2. The process of claim 1, wherein the cyclic imide obeys the general formula (III):

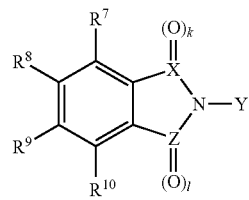

(III)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH and $NO_2$ or from the atoms H, F, Cl, Br and I;

each of X and Z is independently selected from C, S, $CH_2$, N, P and elements of Group 4 of the Periodic Table;

Y is O or OH;

k is 0, 1, or 2; and l is 0, 1, or 2.

3. The process of claim 1, wherein the cyclic imide comprises N-hydroxyphthalimide.

4. The process of claim 1, wherein the contacting is conducted at a pressure below 300 kPa.

5. The process of claim 4 wherein the pressure is between 50 kPa and 200 kPa.

6. The process of claim 1, wherein the contacting is conducted at a temperature of between 50° C. and 130° C.

7. The process of claim 1, wherein the oxygen-containing gas comprises up to 21 volume % oxygen.

8. The process of claim 1, wherein a stripping gas is passed through the reaction medium during the contacting.

9. The process of claim 8, wherein the stripping gas is the same as the oxygen-containing gas.

10. The process of claim 8, wherein the stripping gas is different from the oxygen-containing gas and is inert to the reaction medium and the cyclic imide catalyst.

11. The process of claim 1, wherein the reaction medium is agitated during the contacting.

12. The process of claim 1 and further comprising converting the hydroperoxide phenol and cyclohexanone.

13. The process of claim 12 further comprising dehydrogenating the cyclohexanone to produce further phenol.

14. The process of claim 12 and further comprising converting the phenol produced into bisphenol A.

15. The process of claim 1, wherein the organic acids have from 2 to 4 carbon atoms.

\* \* \* \* \*

UNITED STATES PATENT AND TRADEMARK OFFICE
CERTIFICATE OF CORRECTION

| | | | |
|---|---|---|---|
| PATENT NO. | : | 8,658,836 B2 | |
| APPLICATION NO. | : | 12/678419 | |
| DATED | : | February 25, 2014 | |
| INVENTOR(S) | : | Benitez et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 496 days.

Signed and Sealed this

Twenty-ninth Day of September, 2015

Michelle K. Lee
*Director of the United States Patent and Trademark Office*